(12) United States Patent
Park et al.

(10) Patent No.: US 8,649,847 B1
(45) Date of Patent: Feb. 11, 2014

(54) STEERABLE SHAPE SENSING BIOPSY NEEDLE AND CATHETER

(75) Inventors: Yong-Lae Park, Stanford, CA (US); Richard James Black, Menlo Park, CA (US); Behzad Moslehi, Los Altos, CA (US); Mark R. Cutkosky, Palo Alto, CA (US); Santhi Elayaperumal, Stanford, CA (US); Bruce Daniel, Stanford, CA (US); Alan Yeung, Stanford, CA (US); Vahid Sotoudeh, Los Altos, CA (US)

(73) Assignee: Intelligent Fiber Optic Systems, Inc., Santa Clara, CA (US)

( * ) Notice: Subject to any disclaimer, the term of this patent is extended or adjusted under 35 U.S.C. 154(b) by 871 days.

(21) Appl. No.: 12/562,855

(22) Filed: Sep. 18, 2009

Related U.S. Application Data

(60) Provisional application No. 61/175,399, filed on May 4, 2009.

(51) Int. Cl.
*A61M 25/00* (2006.01)

(52) U.S. Cl.
USPC ......... 600/433; 600/434; 600/435; 604/95.05

(58) Field of Classification Search
USPC ......... 600/372–374, 381, 393, 433–435, 585; 604/95.01, 95.04, 95.05, 96.01, 97.01, 604/98.01, 99.01, 101.01, 101.02; 606/78
See application file for complete search history.

(56) References Cited

U.S. PATENT DOCUMENTS

| | | | | |
|---|---|---|---|---|
| 5,152,748 | A | * | 10/1992 | Chastagner ............... 604/95.05 |
| 5,158,540 | A | * | 10/1992 | Wijay et al. ................. 604/43 |
| 6,256,090 | B1 | * | 7/2001 | Chen et al. .................. 356/73.1 |
| 6,751,367 | B2 | * | 6/2004 | Moslehi et al. .............. 385/13 |
| 2004/0067000 | A1 | * | 4/2004 | Bates et al. ................. 385/7 |
| 2006/0013523 | A1 | * | 1/2006 | Childers et al. ............. 385/12 |
| 2006/0045408 | A1 | * | 3/2006 | Jones et al. ................. 385/12 |
| 2007/0156019 | A1 | * | 7/2007 | Larkin et al. ............... 600/104 |
| 2007/0265503 | A1 | * | 11/2007 | Schlesinger et al. ....... 600/182 |
| 2009/0099551 | A1 | * | 4/2009 | Tung et al. ................. 604/530 |
| 2009/0287092 | A1 | * | 11/2009 | Leo et al. ................... 600/474 |

* cited by examiner

*Primary Examiner* — Rene Towa
(74) *Attorney, Agent, or Firm* — File-EE-Patents.com; Jay A. Chesavage

(57) ABSTRACT

A biopsy needle has a central axis and includes one or more sensing regions, each sensing region formed by a plurality of sensing optical fibers located over a particular extent of said central axis and inside the outer shell of the needle. The sensing optical fibers are coupled to a wavelength interrogator. A steerable catheter has a central axis and outer shell, the outer shell coupled to a plurality of optical fibers in sensing regions and actuation regions, the sensing regions formed over particular extents of the central axis by bonding gratings to the inner surface of the outer shell, and the actuation regions formed by coupling optical energy into shape memory alloys bonded to the outer shell.

17 Claims, 9 Drawing Sheets

Force Sensing Catheter body

Force Sensing (120°)
Catheter body (section A-A)

Force Sensing (90°)
Catheter body (section A-A)

Force Sensing Steerable Catheter body

Force Sensing Catheter body (B-B)

SMA bending Catheter body (B-B)

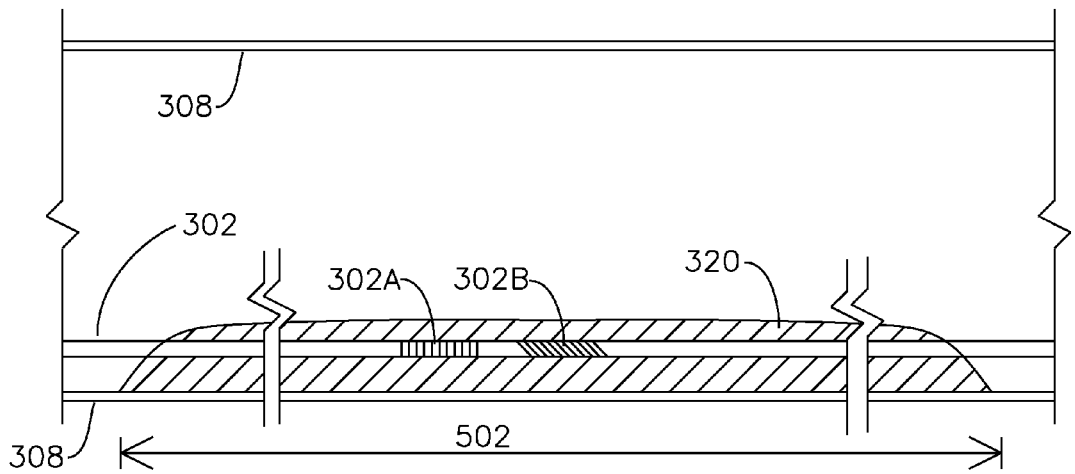
*Figure 5*
Section C-C
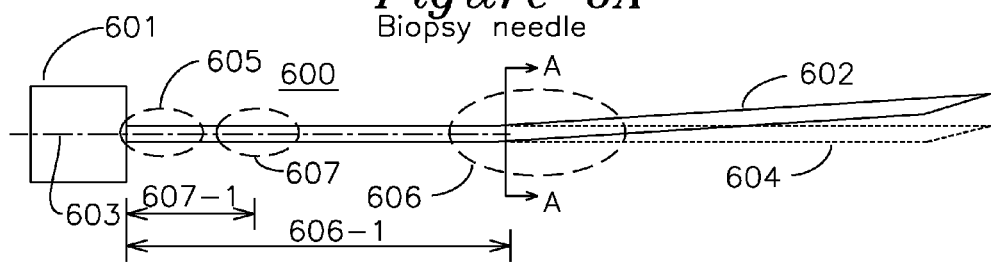
*Figure 6A*
Biopsy needle
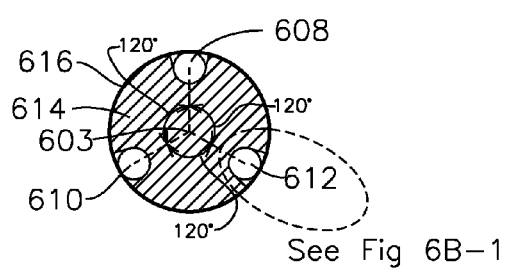
*Figure 6B*
Magnified Section A-A of Figure 6A
*Figure 6B-1*
Groove detail Acutation & Shape Sensing Shape Sensing Section B-B Actuation Section C-C Shape Sensing Section D-D Force Loading and Unloading Test Needle Bending with FBG attached
front view Needle Bending with FBG attached
top view All Optical Measurement & Deflection System Texture Sensing Catheter Stiffness vs Resonant Frequency Response vs Frequency

STEERABLE SHAPE SENSING BIOPSY NEEDLE AND CATHETER

PRIORITY CLAIM

The present patent application claims priority of U.S. Provisional Patent Application 61/175,399 filed May 4, 2009.

This invention was made with government support under: NIH Phase I SBIR grant number 1R43HL092771-01, "Fiber Optic Sensorized Tools for Cardiology Applications", and the USAMRAA Phase I STTR Contract No.: W81XWH-08-C-0103, "MRI-Compatible Fiber-Optically Sensorized Surgical Tools for Precision Removal of Solid Tumors". The government has certain rights in this invention.

FIELD OF THE INVENTION

The present invention relates to a biopsy needle, and is extendable to a catheter. In particular, the invention is related to a biopsy needle which can be steered while entering the body as well as after entering the body, and which generates an optical measurement which can be read and converted to an estimate of needle shape and optionally location using a strain-sensitive optical grating. A needle with such properties is of use in Magnetic Resonance Imaging (MRI) settings which are sensitive to disturbances in the magnetic field generated by prior art sensors located on a needle.

BACKGROUND OF THE INVENTION

The manipulation of needles through tissue, catheters through blood vessels, and other minimally invasive devices which reach targets in the body is the initial step of nearly all MRI-guided interventions. To date, most research on MRI targeting has focused on using MRI to image the target, and to plan the trajectory of interventional devices. During the subsequent manipulation, however, it is useful to track any deviation from the planned trajectory to minimize positioning error and procedural complications. Previous techniques for tracking devices include rapid MRI, MR-tracking, and gradient-based tracking ("Endoscout®", Robin Medical Inc). These methods are all limited because they require use of the MRI system during manipulation, require the device to be within the homogeneous volume of the gradient fields used for imaging, and because susceptibility artifacts from MRI-compatible metallic devices may cause distortions that lead to poor signal and/or inaccurate position information. The latter two tracking methods also require integration of an electronic apparatus into the interventional devices, which further increases device complexity including adding the need for appropriate patient isolation electronics.

Additionally, in the prior art, a catheter which is guided through blood vessels is not able to indicate the state of roughness of the interior lumen of the vessel, and it would be desired to provide a measure of roughness of the lumen.

In one prior art catheter, a series of cables are used to steer the catheter, such as through a bifurcation in the blood vessels.

OBJECTS OF THE INVENTION

A first object of this invention is a shape sensing biopsy needle which has a plurality of optical fibers with fiber Bragg gratings (FBGs) arranged co-axially about a central axis and adjacent to the outer surface of the biopsy needle, such that deflections in the biopsy needle result in sensor strain which can be measured in a remote optical interrogator to estimate needle deflection.

A second object of the invention is a steerable biopsy needle which has a plurality of optical fibers disposed circumferentially about a center axis, the optical fibers each having at least one strain grating and an adjacent angled deflection grating, the deflection grating for coupling optical energy out of an optical fiber and into a shape memory alloy (SMA), and the strain grating for measuring a resulting strain or deflection generated by the excited SMA.

A third object of the invention is a shape sensing catheter having a plurality of optical fibers, each with a strain sensor, the optical fibers disposed circumferentially about the central axis of the catheter, the optical fibers having gratings which are bonded to an outer shell of the catheter such as with cyanoacrylate adhesive, the sensors detecting deflection of the catheter and reporting the strain with an FBG sensor and external optical interrogator, thereby determining the position of the catheter.

A fourth object of the invention is a catheter which has a plurality of optical fibers arranged circumferentially about a central axis, each optical fiber having a strain grating for measurement of catheter deflection, and also a set of deflection gratings proximal to and on the same fiber as the strain gratings, where the deflection gratings include an angled grating which couples high power optical energy at a wavelength separate from the strain grating wavelength into an adjacent shape memory alloy (SMA), such that the SMA contracts along a line coaxial to the catheter shell, thereby causing the deflection of the catheter in a controlled manner such as by using 90 degree or 120 degree azimuthal separation between actuators, with the deflection grating of the corresponding fiber having the angled grating forming a measurement of the resultant deflection.

A fifth object of the invention is a texture sensing catheter having one or more contact ridges which couple vibrations generated by movement of the contact ridge over a surface to be measured, thereby providing for the measurement of surface roughness.

A sixth object of the invention is a stiffness sensing catheter having a source of vibration and a measurement sensor coupled to the central axis of a catheter, the measurement sensor converting measured vibration frequency to a stiffness measurement.

SUMMARY OF THE INVENTION

In a biopsy needle embodiment of the invention, Fiber Bragg Grating (FBG) sensors reflect optical energy with a peak wavelength that shifts in proportion to the strain to which a particular FBG is subjected. The advantage of optical devices such as sensors and actuators which rely on optical fiber is they are inherently MRI-compatible, do not interact with the MRI image acquisition process, and do not cause significant imaging artifacts, thereby providing an ideal method of sensing the configuration and forces upon interventional devices in the MRI environment. FBG strain sensors of the present invention can resolve strains as small as 0.1 micro-strain and multiple FBG sensors can be located along a single fiber and addressed via optical multiplexing. In one embodiment of the present invention, FBG sensors are placed circumferentially about, and parallel to, the central axis, and strain gratings in the fibers are used to detect the deflection of a needle such as a biopsy needle for use in an MRI environment.

In a second embodiment of the invention, a steerable biopsy needle has an inner fiber locator (or inner guide) having a plurality of axial grooves parallel to a central axis and disposed circumferentially about an outer diameter adjacent to an outer needle sleeve which surrounds the inner fiber locator, the axial grooves for restraining an optical fiber, the optical fiber of each groove having a strain sensor comprising a fiber Bragg grating (FBG) bonded to the inner guide, where the inner guide is placed inside, but removable from, the outer needle sleeve such that the inner guide and outer sleeve may be inserted and guided into the tissue region together, and after placement and optional steering to a desired location, the inner guide may be withdrawn from the outer needle sleeve such that a biopsy sample from the located tissue may be taken. In a steerable embodiment, each optical fiber also has an angled deflection grating which couples optical energy from a high power optical source to a shape memory alloy (SMA) which is in contact with the outer needle sleeve, thereby providing a mechanism for steering the needle by coupling optical energy from the fiber to the SMA using the angled deflection grating, while the needle shape or displacement is measured by the strain sensor grating.

The biopsy needle may have a plurality of strain sensors, and which may optionally incorporate actuation gratings for needle deflection sensing, is suitable for use in MRI-guided percutaneous needle biopsy and brachytherapy, in which MRI is used to plan needle placement, but is limited in accuracy during insertion due to needle deflections that commonly occur.

In a third embodiment of the invention, a steerable catheter has an outer shell having a central axis, and the outer shell has a plurality of optical fibers placed parallel to the central axis and circumferentially about the diameter of the outer shell. An inner surface of the outer shell has a plurality of axial optical fibers which are bonded such that deflection of the outer shell may be sensed using an optical interrogator.

In a fourth embodiment of the invention, a steerable catheter has an outer shell having a central axis, and the outer shell has a plurality of optical fibers placed parallel to and circumferentially about the diameter of the outer shell. The outer shell has a plurality of axial optical fibers which are bonded to the outer shell, and each fiber has a sensing fiber for measuring a stress of the outer shell using a fiber Bragg grating (FBG) and also an angled grating for directing optical energy to a shape memory alloy (SMA).

In a fifth embodiment of the invention, a catheter has a tip with one or more circumferential convex grooves formed in the exterior of a hemispherical surface. The convex grooves make contact with and move across the interior surface of a passageway, thereby creating vibrations which are sensed by a vibration sensor in the catheter, which vibrations are converted to electrical signals and transmitted to a remote receiver.

BRIEF DESCRIPTION OF THE DRAWINGS

FIG. 5 shows the section C-C of FIG. 4B.

FIG. 6A shows a biopsy needle having deflection with internal fiber Bragg grating sensors measuring the deflection.

FIG. 6B shows a cross sectional view of the biopsy needle of FIG. 6A.

FIG. 6B-1 shows a detail view of FIG. 6B.

DETAILED DESCRIPTION OF THE INVENTION

One aspect of the invention incorporates a plurality of optical fibers with fiber Bragg gratings (FBG) placed co-axially to form an MRI compatible biopsy needle, and in one embodiment, the outer needle sleeve 616 is a stock 18 gauge diameter×15 cm long biopsy needle, such as E-Z-EM model MR 1815, with an inner fiber locator 614 inserted in the needle sleeve 616 for guiding and shape sensing, which is removed for biopsy sampling. The FBG strain sensor can be located close to the base, where strain is concentrated in bending, or in another embodiment of the invention, the strain sensors can be in one or more axial extents and distributed circumferentially about the central axis and adjacent to an external sheath of the needle. In one embodiment of the invention, a first set of sensors is located a first distance from the needle base, and a second set of sensors is located a second distance from the needle base. In another embodiment of the invention, a series of FBGs are used as temperature sensors and provide temperature sensing information which is used to correct the strain sensor measurements.

Figure 1:
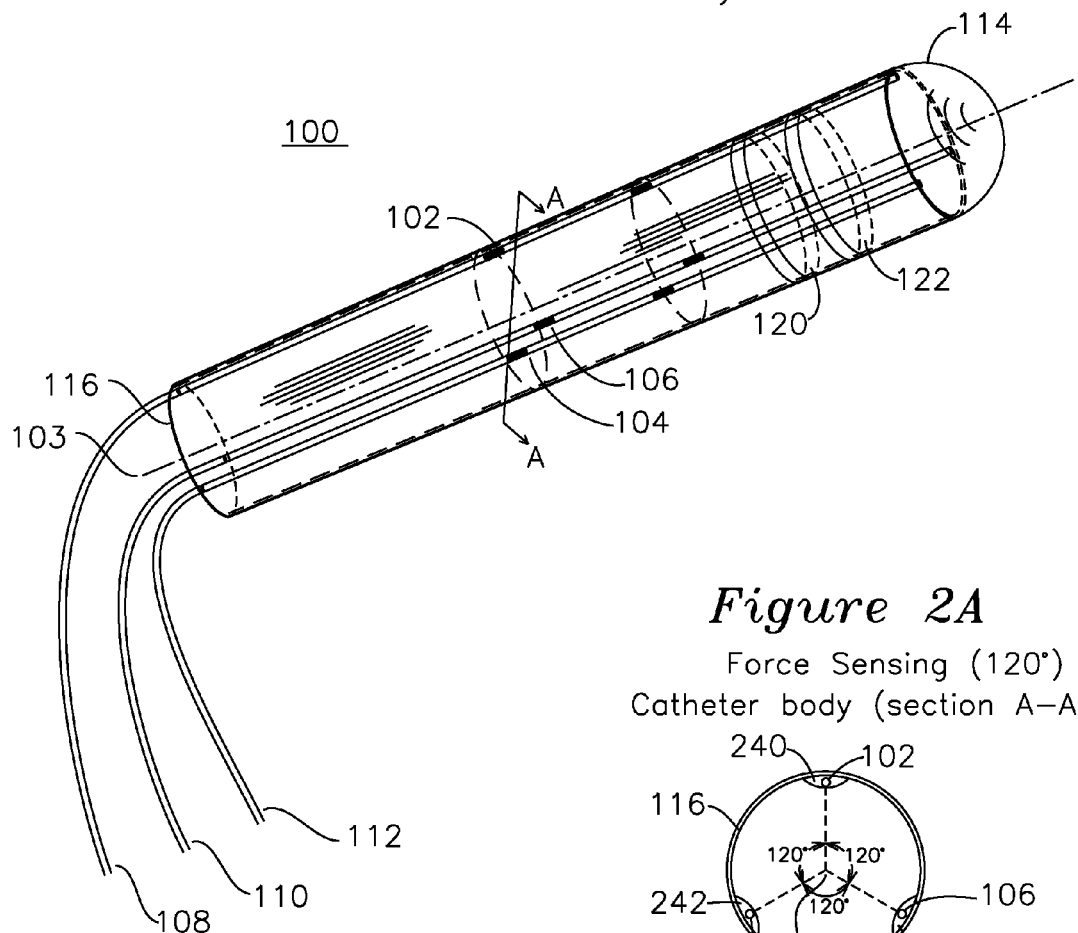
FIG. 1 shows a perspective view of a shape sensing catheter.

FIG. 6A shows a biopsy needle 600 with an original shape 604 and a deflected shape 602. If fiber Bragg grating sensors are positioned circumferentially about the central axis 603 of the needle with a substantially equal included angle such as an included angle of either 120 degrees or 90 degrees, then deflection of the needle may be measured. In one embodiment of the invention, the FBG sensors are formed in single-mode or few-mode optical fiber, and the gratings are placed in the body of the needle such as in region 606, such that these strains may be measured externally, and an estimate of needle position can be made using strain measurements of the three fiber optic Bragg gratings over a particular axial extent 606. In another embodiment of the invention, the sensors are placed in a base region 605 adjacent to a fixed needle mount 601 (deflection not shown). In an embodiment for two region measurement in a biopsy needle having a length of 15 cm and a diameter of 18 gauge, a first measurement region 607 having FBGs is located a distance 607-1 of 22 mm from the base 601, and a second measurement region 606 having FBGs positioned on the same fiber is located a second measurement distance 606-1 of 85 mm from the base 601. A cross section A-A of the needle 600 is shown in FIG. 6B. A removable outer sheath 616 surrounds a fiber locator 614 which has a plurality of grooves which contain fibers 608, 610, and 612, and locator 614 provides an angular spacing about central axis 603 such as 120 degrees (as shown), 90 degrees, or any substantially equal included angle with respect to the central axis 603 of the outer shell 616 that provides orthogonality of deflection measurement. Each grating is disposed over a particular axial extent for the sensing of strains in that extent. FIG. 6B-1 shows a detail view of one of the grooves of FIG. 6B, including fiber bonding agent 613 such as cyanoacrylate which supports fiber 612 in an associated groove.

Figure 6C:
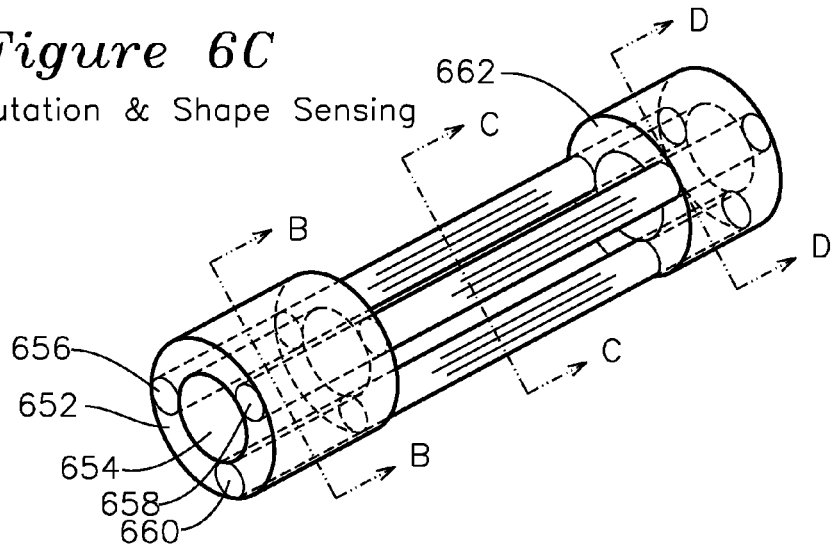
FIG. 6C shows a perspective view of an example needle actuator and shape sensor
Figure 6D:
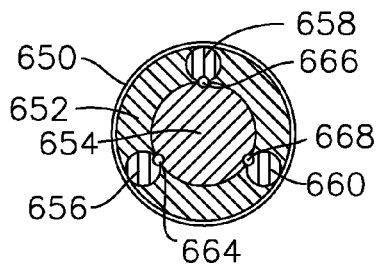
FIG. 6D shows a cross section view of the shape sensing section of FIG. 6C.
Figure 6E:
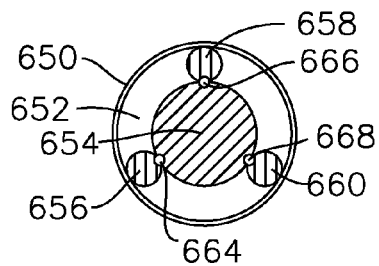
FIG. 6E shows a cross section view of the actuation section of FIG. 6C.
Figure 6F:
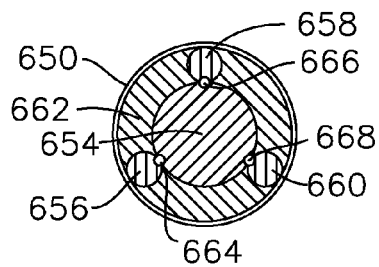
FIG. 6F shows a cross section view of the shape sensing section of FIG. 6C.

Another example embodiment of the biopsy needle is shown in FIG. 6C (with outer needle sheath 650 removed for clarity), and is best understood in combination with section view B-B of FIG. 6D, section view C-C of FIG. 6E, and section view D-D of FIG. 6F. An inner support core 654 is surrounded by SMA rods 656, 658, and 660, and the SMA rods and inner support 654 are captured by first support 652 and second support 662 which form a deflection region, with an outer needle sheath 650 enclosing the entire assembly. The rods 656, 658, and 660 are thermally actuated by heat developed in the rods by coupling optical energy from adjacent optical fibers 664, 666, and 668 in the deflection region. Each optical fiber 664, 666, and 668 has an angled grating for coupling energy out of the fiber and to the adjacent SMA, with the preferred angle being 45 degrees with respect to the optical fiber axis, and the angled gratings written using any technique such as interferometry, and the optical fibers which contain the optical gratings being either single-mode, few-mode, or multi-mode fibers, as is known in the art. The SMA rods 656, 658, 660 are unconstrained in the region of section C-C of FIG. 6C, and in contact with and receiving optical energy from angled gratings of nearby corresponding optical fibers 664, 666, and 668, which fibers are captured in grooves between the inner support core 654 the corresponding SMA rod 656, 658, and 660. Shape sensing gratings may be positioned in the region of section C-C which measures the strain of the corresponding fiber. As an example of actuation, in one embodiment, the three SMA rods 656, 658, 660 have convex shape (when not de-activated by thermal energy coupled from the optical fiber) toward the central axis when unconstrained by end supports 650 and 662. When the end supports constrain the ends of the rods, the bending force of each SMA rod cancels the forces of the other rods, and the structure is in equilibrium and straight. If remaining rods 656 and 660 are heated to an SMA activation temperature, the force cancellation no longer occurs, and the needle body will tend to the unconstrained shape of rod 658. This is only one example of the placement of the SMAs in the needle body for shape actuation, and many others are possible.

Suitable materials for the device shown in FIGS. 6A, 6B, 6C, 6D, 6E, and 6F for MRI applications include the non-magnetic materials nickel-chromium-molybdenum alloy (such as Inconel 625) for the inner fiber locator structure 614, nickel-cobalt-chromium-molybdenum alloy (such as MP35N) for the outer needle sheath structure 616 and 650, or the inner support core 654, end supports 652 and 662, and the outer sheath 650 structures may be formed from materials such as stainless steel, titanium, or a suitable non-magnetic material consistent with use in an MRI scanner.

Figure 6G:
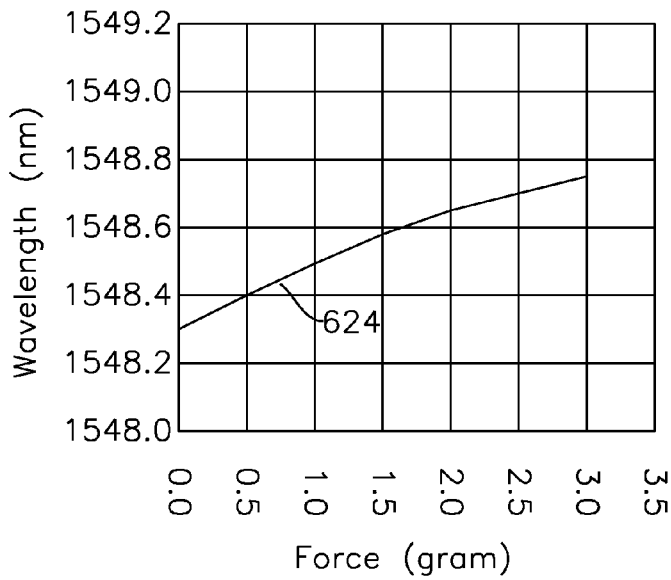
FIG. 6G shows a plot of wavelength shift versus deflection for a biopsy needle.

FIG. 6G shows a wavelength versus force plot for the case where the needle deflection is in a direction defined by a plane which includes the central axis 603 and a particular fiber such as 612 having a grating located in region 605. FIG. 6G curve 624 shows wavelength changes in force loading and unloading of the needle inner fiber locator and outer sleeve which are coupled to the sensing FBG. Based on the characteristic plot for a particular needle grating, the needle tip deflection can be calculated from the sensor signal in the form of wavelength change. In one embodiment of the invention, the needle deflection is restricted to 10% of needle length to maintain linearity of deflection measurement, thereby allowing calculation of needle deflection using small-strain linear beam theory and one, two, or multi-point FBG strain measurement. Alternatively, positional estimation software can incorporate knowledge of the deflection versus wavelength characteristic such as by using a look-up table or curve fitting equation for improved accuracy.

Figure 6H:
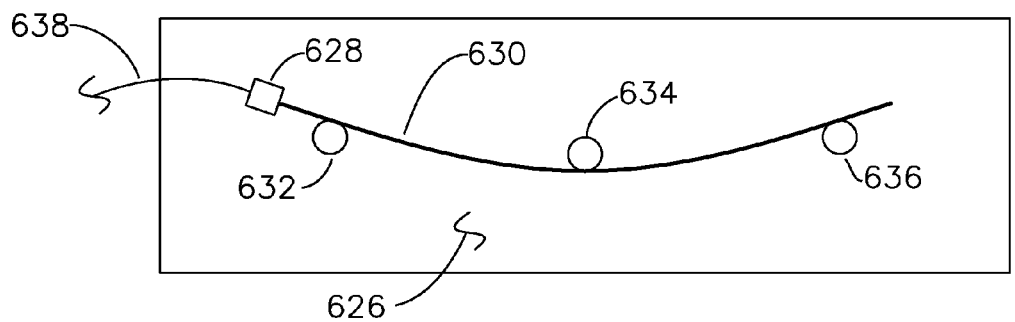
FIG. 6H shows a front view of a biopsy needle in an imaging test phantom.
Figure 6I:
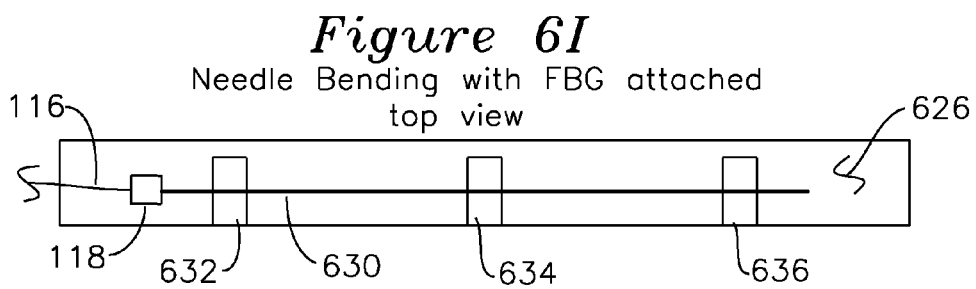
FIG. 6I shows a top view of a biopsy needle in an imaging test phantom.

FIG. 6H shows the front view of an MRI imaging phantom where a contrast fluid such as water 626 is provided in an enclosed chamber with a needle 630 fabricated according to one of the embodiments of the invention such FIG. 6A with sensors located in a region of bending 606. Stops 632, 634, 636 hold the deformed needle in place and enclosed in a water bath, and optical fibers 638 are coupled to an external optical interrogator to measure wavelength shift which may be converted to a positional deflection or strain. FIG. 6I shows a top view of the fixture of FIG. 6H, and when the imaging phantom is placed in an MRI scanner, no artifacts are observed, although the needle and surrounding structures are clearly visible. With biopsy needle of FIG. 6A and an optical interrogator coupled to the fibers 608, 610, and 612 leaving the needle, it is therefore possible to estimate needle position from FBG wavelength measurement with the needle in a magnetic resonance imaging environment without the introduction of MRI artifacts, since the biopsy needle can be formed into standard diameters and lengths, and the optical fiber contains no materials which would generate an MRI response. Although results are presented in FIG. 6G for a single FBG strain sensor, it is clear that three sensors can be interrogated for wavelength to estimate strain, thereby generating an estimate of needle position in 3 axis.

The angled gratings of the deflection region which couple optical energy to thermally activate the SMA may be formed in single-mode fiber, few-mode fiber, or multi-mode fiber. The strain gratings of the sensing region which respond to the strain of deflection may be formed from single-mode or few-mode fiber. In the embodiments shown in the figures, the same optical fiber supports a deflection region and a sensing region such as by series connection, although it is understood that the sensing fiber and deflection fiber may also be distinct fibers of different type and in different locating grooves or with both fibers sharing the same groove, such as by using single-mode fiber for a sensing region and a multi-mode fiber for a deflection region.

Figure 2A:
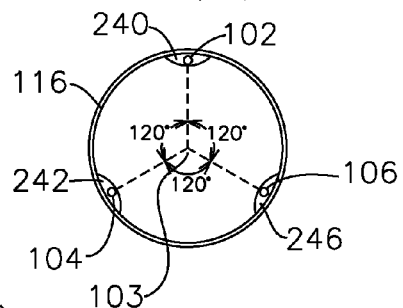
FIGS. 2A and 2B show cross section views of the sensors of FIG. 1 for n=3 and n=4 sensors, respectively.
Figure 2B:
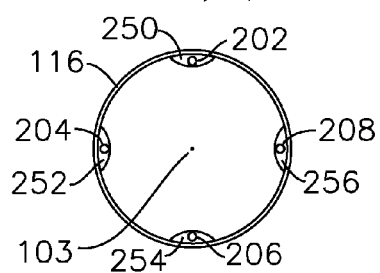

Another embodiment of the invention is the application of strain sensors applied circumferentially to the shell of a catheter for use in navigating through blood vessels. FIG. 1 shows a force sensing catheter body 100, where optical fibers which are placed circumferentially about the shell 116 of the catheter, in a manner similar to what was described for the biopsy needle body 600 of FIG. 6. FIG. 1 shows n=3 gratings 102, 104, 106 positioned circumferentially, and shown in cross section FIG. 2A. FIG. 2B shows the same cross section view for n=4 gratings at 90 degree angular spacings with respect to the central axis 103, and other angular spacings are also possible. For the example, in the n=3 120 degree configuration of FIG. 2A, the gratings 102, 104, 106 are disposed in optical fibers 108, 112, 110, respectively, and are secured to the outer shell 116 of the biopsy needle or catheter using a bonding agent 240, 242, 246, such as epoxy or cyanoacrylate which acts to secure the fibers to the catheter shell 116. The secure attachment of the fibers to the inner surface of shell 116 sufficient to make strain measurements may be performed many different ways, but is shown in the present example for attachment of the grating extent. It is also possible to tension the fiber and attach at end points over extents of the catheter, for example. By having each series grating operative over a separate wavelength, it is also possible to provide a plurality of series fiber Bragg gratings with multiple attachment points or a continuous line of attachment along a single fiber to detect the deflection of the shell in multiple locations, and the shell may be disposed to provide preferential bending at those locations. In the multiple series grating scenario, the catheter is able to provide multiple extent measurement while still using only three fibers 108, 110, and 112.

Figure 7:
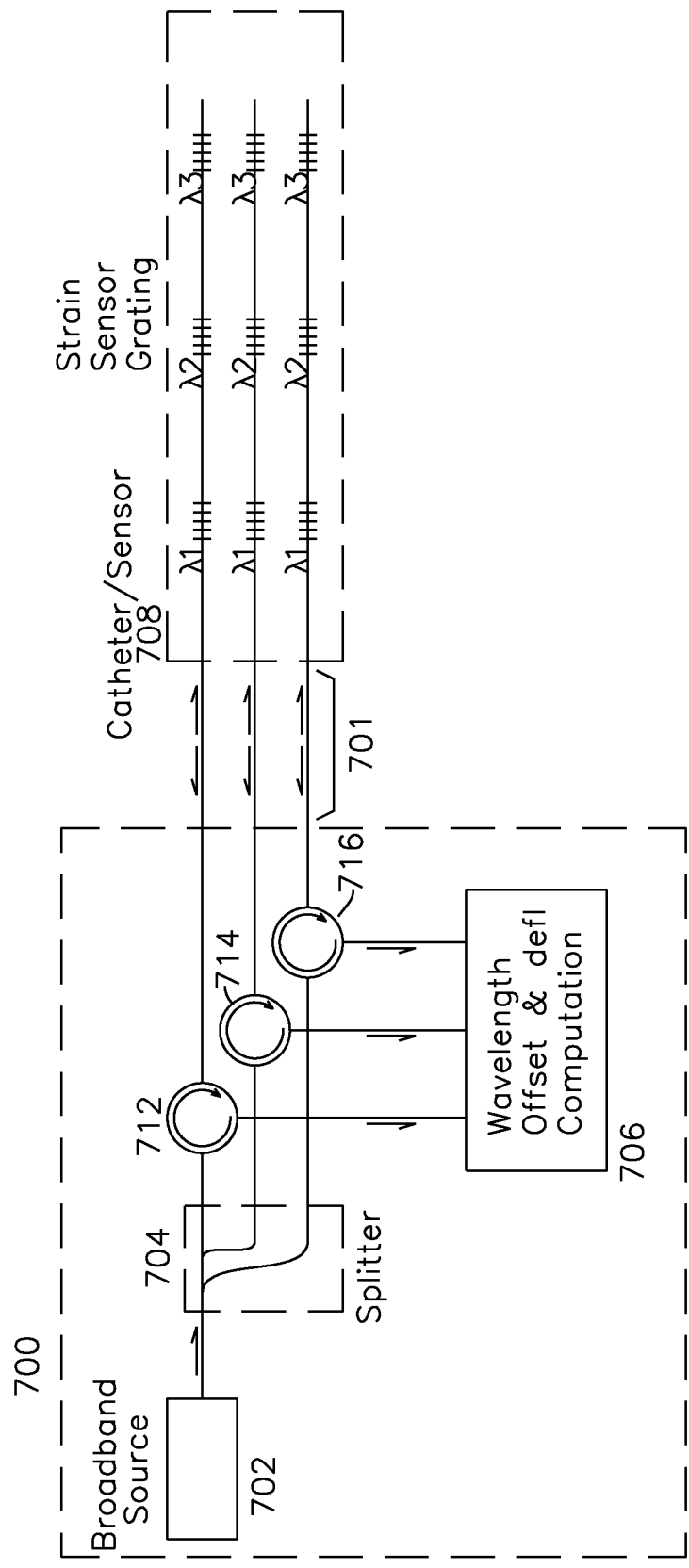
FIG. 7 shows the block diagram for an all optical wavelength interrogator.

FIG. 7 shows a wavelength interrogator 700 for use with the biopsy needle 600 of FIG. 6 or catheter 100 of FIG. 1, which are shown generally as Catheter/Needle 708 and coupled to wavelength interrogator 700 using fibers 701. Wavelength interrogator 700 includes a broadband source 702, a splitter 704, first circulator 712, second circulator 714, and third circulator 716, each circulator coupled to an optical fiber of the catheter or biopsy needle 708, and each grating of the catheter/biopsy needle is responsive to a wavelength within the broadband source 702. Energy at each wavelength is reflected through circulators 712, 714, 716 to wavelength interrogator 706, which measures the wavelength of reflected optical energy in each grating, converts these wavelength measurements to a strain, and then estimates the position of the needle from those strains, using the elasticity of the needle or catheter shell 116 to determine the displacement of the needle, such as displacement 602 from normal position 602 of FIG. 6.

Figure 3:
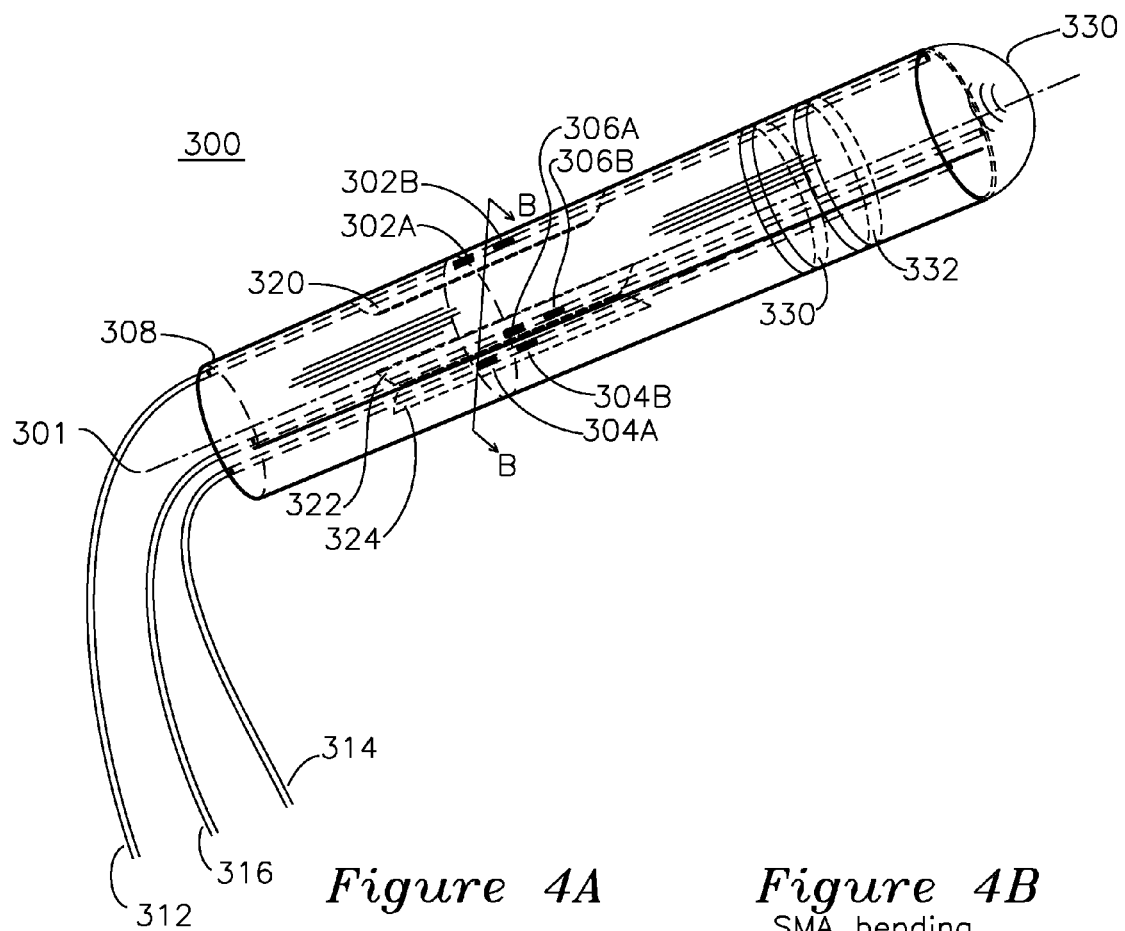
FIG. 3 shows a shape sensing steerable catheter body perspective view.
Figure 4A:
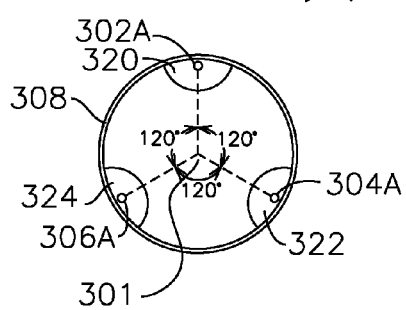
FIGS. 4A and 4B show a cross section of FIG. 3 for 120 degree sensor separation of a sensor region and deflection region, respectively.

Another embodiment of the invention is shown in FIG. 3 which combines the force sensing of FIG. 1 for estimation of position combined with the new function of steering the catheter using a remote optical source. The steering can be done any number of ways which generate differential force on the outer shell of the catheter. In one embodiment shown in the FIG. 4A cross section of FIG. 3, the optical fibers are secured to the inside surface of the catheter shell 308 as before, and sensing regions are formed using the optical fibers which include Bragg gratings 302A, 304A, 306A with the Bragg gratings bonded 320, 322, 324, respectively, using epoxy or cyanoacrylate, to the inside of flexible shell 308. The optical fibers are separated by 120 degrees or 90 degrees, as was described for FIGS. 2A and 2B, respectively, with FIG. 2B showing n=4 fibers 202, 204, 206, 208 secured by corresponding respective bondings 250, 252, 254, 256. In a deflection region of the optical fiber adjacent to the sensing region formed by strain gratings 302A, 304A, 306A of section view of FIG. 4A are the corresponding angled deflection region actuation gratings 302B, 304B, 306B shown in cross section FIG. 4B, where each actuation grating couples optical energy 326 into the adjacent shell 308 formed from SMA material with the angled grating region of fibers 302B, 304B, 306B bonded 320, 322, 324 to the shell 308. Alternatively, the angled gratings 302B, 304B, 306B may couple optical energy 326 into linear wires formed from SMA (not shown) coaxial to fiber 302 which are embedded in epoxy 320. The property of the SMA is such that it exerts a bending force until heated to a critical temperature, after which it loses its spring property, and the heating effect is achieved using optical energy coupled out of special angled gratings 302B, 304B, 306B which are adjacent to the corresponding SMA. It is possible to create multiple regions of sensing by having the sensing FBGs operative at separate wavelengths, and it is possible to have multiple regions of actuation by having the angled gratings which couple optical energy out of the fiber operative at unique wavelengths as well. In this manner, sets of sensing and actuation gratings can operate together to deflect (actuate) and measure the deflection (shape) of the catheter in a very flexible and separable manner. The three main types of shape memory alloys (SMA) are copper-zinc-aluminum-nickel, copper-aluminum-nickel, and nickel-titanium (NiTi) alloys. NiTi alloys are generally more expensive and change from austenite to martensite upon cooling. The transition from the martensite phase to the austenite phase is only dependent on temperature and stress, not time, as there is no thermal diffusion involved. Similarly, the austenite structure gets its name from steel alloys of a similar structure. It is the reversible diffusionless transition between these two phases that allow the special properties to arise. While martensite can be formed from austenite by rapidly cooling carbon-steel, this process is not reversible, so steel does not have shape memory properties. The angled gratings of the deflection region which couple optical energy to thermally activate the SMA may be formed in single-mode fiber, few-mode fiber, or multi-mode fiber. The strain gratings of the sensing region which respond to the strain of deflection may be formed from single-mode or few-mode fiber. In the embodiments shown in the figures, the same optical fiber supports a deflection region and a sensing region such as by series connection, although it is understood that the sensing fiber and deflection fiber may also be distinct fibers of different type, such as single-mode fiber for a sensing region and a multi-mode fiber for a deflection region.

Figure 4B:
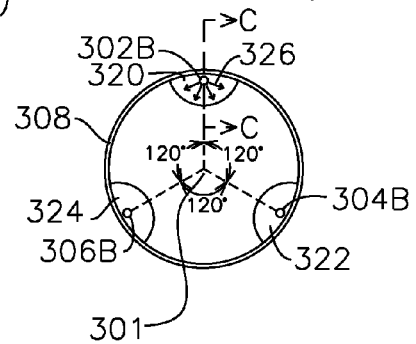

FIG. 5 shows a magnified cross section view of axial section C-C of FIG. 4B, showing optical fiber 302, which is attached to catheter shell 308 using a bonding agent 320 such as cyanoacrylate to secure strain grating 302A and angled grating 302B, which couples high power optical energy to shell 308 which may be formed from SMA, or linear wires formed from SMA (not shown) coaxial to fiber 302 which are embedded in epoxy 320. The strain grating 302A, actuation grating 302B and bonding agent 320 are operative over an axial extent 502 of the catheter.

Figure 8:
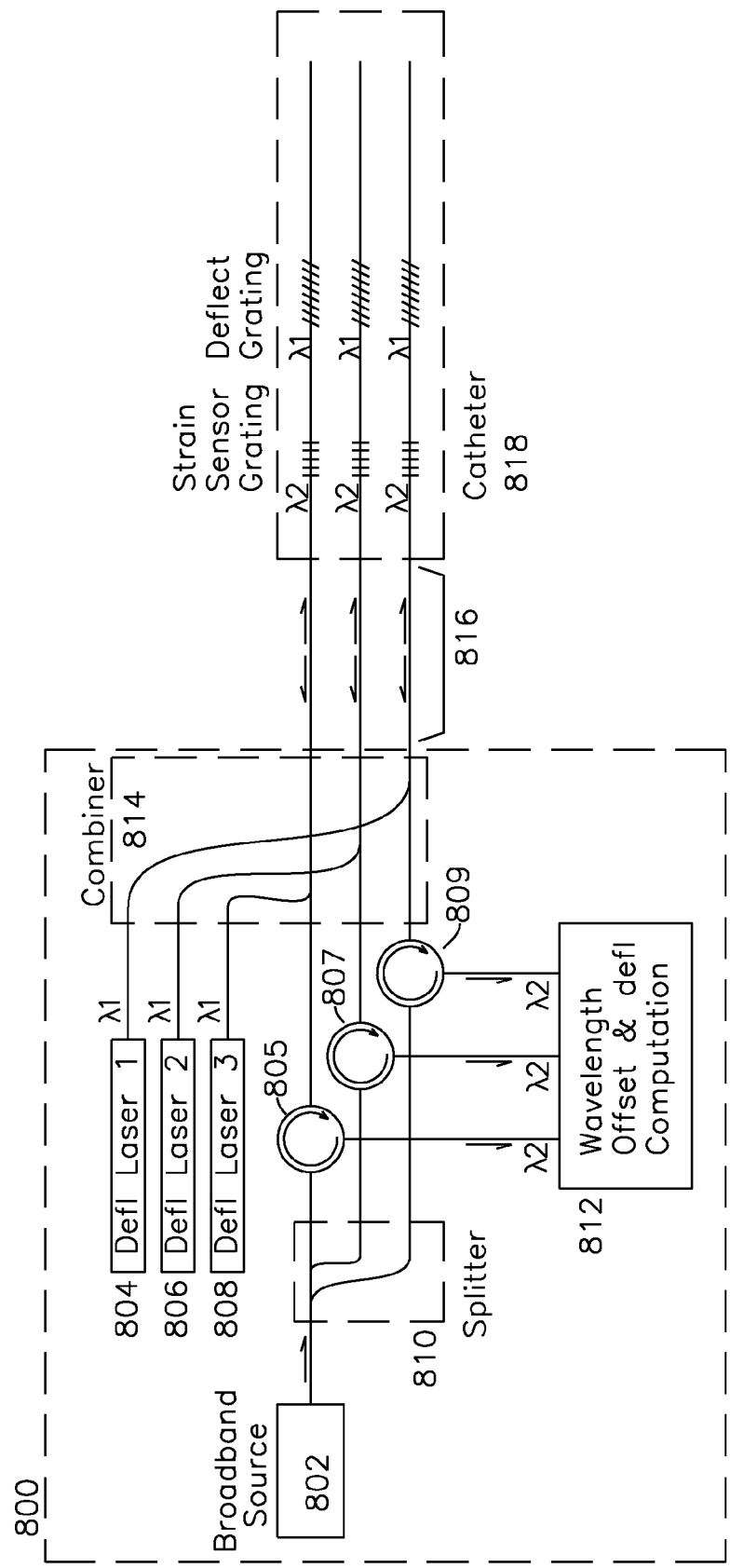
FIG. 8 shows the block diagram for an all optical wavelength interrogator with SMA excitation laser and gratings.

FIG. 8 shows an example of an all optical measurement and actuation system according to the present invention. Optical interrogator 800 is coupled to the Catheter/needle assembly 818 through optical cables 816. For strain measurement, the optical interrogator 800 has a broadband source 802 which is coupled to splitter 810 and to circulators 805, 807, and 809, through fiber optic cables 816 and to catheter/needle strain sensors at wavelength λ2. Reflected optical energy at wavelength λ2 is coupled from circulators 805, 807, 809, and to wavelength offset and deflection computation engine 812, which converts wavelength shift into positional information. High power actuation lasers 804, 806, 808 couple optical energy at wavelength λ2 through combiner 814 to the respective fibers of catheter 818, and to angled gratings which are responsive to optical energy at wavelength λ1, and couple optical energy at λ1 out of the optical fiber and into the SMA.

The catheter tip 114 of FIGS. 1 and 330 of FIG. 3 may have an outer surface which is hemispherical, convex, or any shape suitable for guidance of the catheter along a passageway such as a blood vessel. Additionally, the catheter 100 of FIG. 1 or 300 of FIG. 3 may include electrodes 120 and 122, and 330 and 332, respectively, for measurement of a physiological phenomenon such as an electro-cardiogram (EKG), or alternatively for the application of a current such as for ablation of nearby tissue. The cylindrical body or convex tip of the catheter may also include structures for anchoring the catheter. In one embodiment of the invention, anchoring may be accomplished using inflatable balloons (not shown) and tubing (not shown), with the inflatable balloons placed along one or more sides of the catheter and inflated after positioning of the catheter such as for either anchoring the catheter in place, or for therapeutic purposes such as angioplasty.

Figure 9:
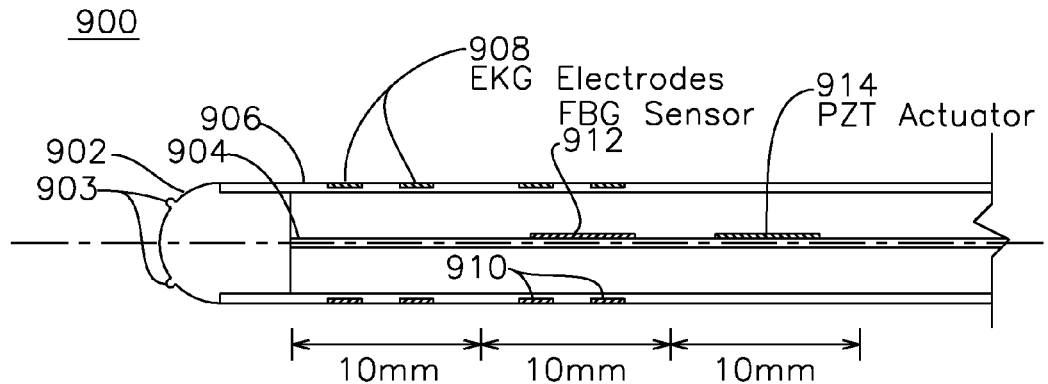
FIG. 9 shows a texture sensing catheter.
Figure 10:
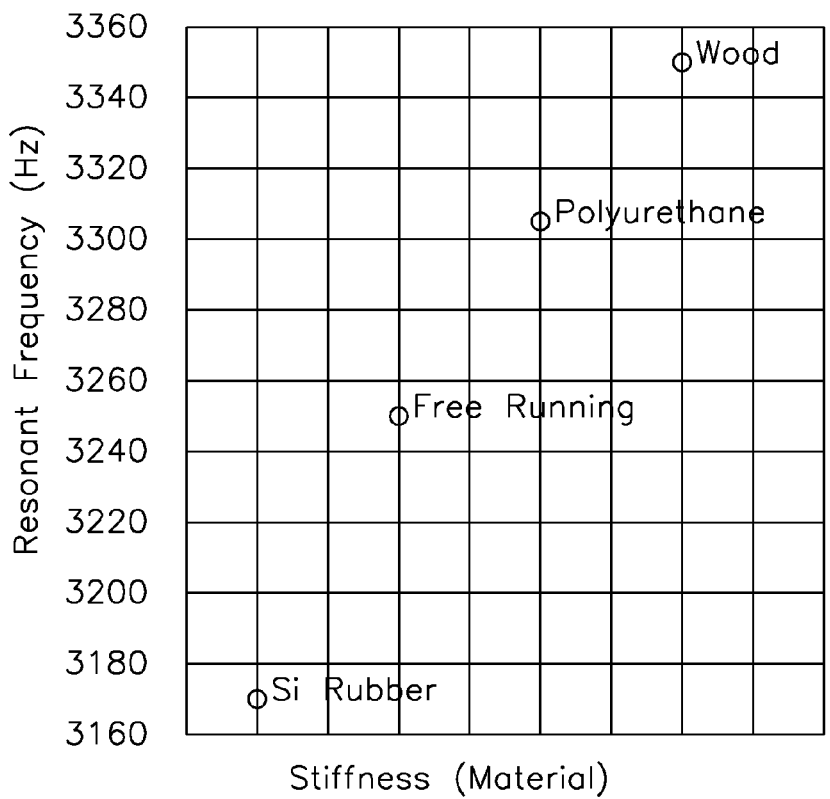
FIG. 10 shows a point plot of stiffness versus resonant frequency.
Figure 11:
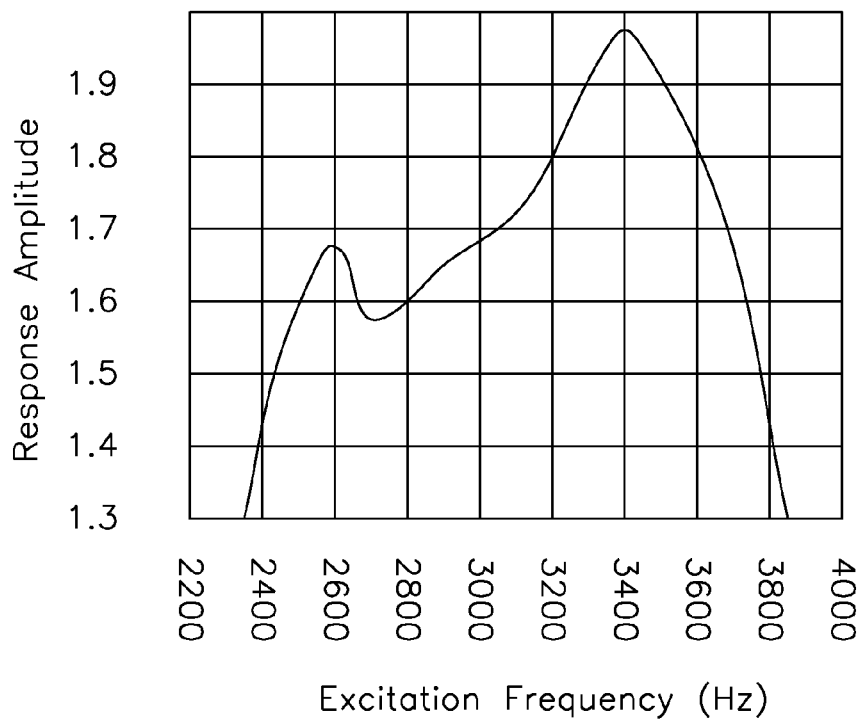
FIG. 11 is a plot of amplitude vs frequency.

FIG. 9 shows another embodiment of the invention for cardiac use and measurement of cardiac lumen tissue, where a texture sensing catheter has a tip 902 with an annular ridge 903, as well as EKG ring leads 908 coupled to an EKG monitor. When the ridge 903 of tip 902 is guided over a surface to be characterized for roughness, the movement of the annular ridge 903 over the surface causes a vibrational deflection of the catheter tip 902, which is attached to a central support 904 having FGB sensors 912 which are responsive to vibration in the central post 904. In this manner, vibrations are coupled to sensor 912 and read as wavelength changes and converted to a time domain signal. In another embodiment of the invention, a PZT actuator 914 generates a mechanical excitation which is mechanically coupled to the probe tip 902, and to tissue in contact with the tip (not shown), whereby the stiffness of the tissue modifies the frequency range of the returned acoustic energy generated by actuator 914. FIG. 10 shows an example of stiffness versus resonant frequency for various materials. By observing the change in resonant frequency, it is possible to estimate the stiffness of the material in contact with the catheter, thereby providing a tissue characterization result which can discern between diseased tissue and healthy tissue. FIG. 11 shows a graph of the resonant frequency versus frequency of excitation, which characterization is also useful for tissue characterization.

The examples shown for the sensing needle, steerable needle, sensing catheter, and steerable sensing catheter are provided for understanding of the elements of the invention, and are not intended to limit the scope of the invention, which is set forth in the following claims:

We claim:

1. A force sensing steerable catheter having:
    a substantially cylindrical outer shell having a central axis;
    a convex tip attached to one end of said outer shell;
    a closure attached to the opposite end of said outer shell;
    a plurality of optical fibers bonded to the inner surface of said outer shell;
    one or more sensing regions in said outer shell, each of said one or more sensing regions operative over a central axis extent, each of said one or more sensing regions having a grating formed in each of said optical fibers, each of said gratings bonded to an inner surface of said outer shell where each of said gratings is operative substantially parallel to said central axis and each of said gratings is located in a substantially equal included angle with respect to said axis and to any other of said gratings;
    each of said one or more sensing regions adjacent to a deflection region comprising an actuation optical fiber having an angled grating which directs optical energy in said actuation optical fiber into an adjacent shape memory alloy (SMA), each of said SMAs mechanically coupled to said outer shell;
    a wavelength interrogator coupled to each of said optical fibers, said wavelength interrogator accepting optical energy reflected at particular wavelengths from each of said fibers of said sensing region gratings and converting said reflected optical energy wavelengths for each of said fibers into a sensed shape, said wavelength interrogator also providing optical energy at a wavelength responsive to a corresponding deflection region angled grating for steering said catheter.

2. The steerable catheter of claim 1 where said shape memory alloy is nickel titanium.

3. The steerable catheter of claim 1 where said shape memory alloy includes an optical interface layer for converting optical energy coupled from said angled grating into thermal energy applied to said shape memory alloy.

4. The steerable catheter of claim 1 where said wavelength interrogator includes a first source of optical energy in a wavelength range operative for said sensing region gratings and also a second source of optical energy in a wavelength operative for said angled gratings, said second source of optical energy having a power level sufficient to actuate said shape memory alloy and cause said catheter to deflect.

5. The steerable catheter of claim 1 where each of said deflection region angled gratings is formed in either a single mode fiber or a multi-mode fiber.

6. The steerable catheter of claim 1 where each of said one or more sensing region gratings is formed in either a single mode fiber or a few-mode fiber.

7. The steerable catheter of claim 1 where said wavelength interrogator includes a broadband source coupled to each of said sensing region optical fibers, and each of said sensing region optical fibers is coupled to a circulator for removing reflected optical energy from each of said optical fibers, each of said circulators coupled to a wavelength sensitive detector for converting a wavelength to a differential detector amplitude, said differential detector amplitude converted to a wavelength, with the wavelengths of each of said detectors converted to a positional location of said catheter.

8. The steerable catheter of claim 1 where said tip includes electrodes for the application of a current or the measurement of a voltage.

9. The steerable catheter of claim 1 where said catheter includes one or more balloon regions for anchoring said catheter in a vessel.

10. The catheter of claim 9 where said one or more balloon regions comprises at least two inflatable regions on opposite sides of said catheter.

11. A steerable force sensing catheter having:
    a substantially cylindrical outer shell having a central axis;
    one or more sensing regions in said outer shell, each of said one or more sensing regions formed by an optical fiber having a Bragg grating bonded to said cylindrical outer shell and responsive to a strain or stress in said outer shell;
    each of said one or more sensing regions adjacent to a shape memory alloy (SMA) which receives optical energy coupled to said SMA and causes said SMA to deflect;
    said SMA receiving said optical energy from an optical fiber having angled gratings which directs said optical energy in said optical fiber radially outwards to said SMA;
    whereby an application of said optical energy to an associated SMA causing a deflection of said outer shell, said deflection causes a stress or strain to be coupled to an associated Bragg grating, thereby allowing for control of deflection of said outer shell by said SMA and estimation of deflection of said outer shell by reflection of optical energy from said deflection region Bragg gratings.

12. The steerable force sensing catheter of claim 11 where said one or more sensing regions are formed by optical fibers with said Bragg gratings which are located parallel to said central axis and on an inner wall of said cylindrical outer shell.

13. The steerable force sensing catheter of claim 11 where each sensing region is formed by said Bragg gratings positioned along a single optical fiber, each of said Bragg gratings responsive to a unique range of wavelengths from any another one of said Bragg gratings of said each of said optical fibers.

14. The steerable force sensing catheter of claim 11 where each SMA is located adjacent to said outer shell, each SMA positioned parallel to said coaxial axis.

15. The steerable force sensing catheter of claim 11 where each energy to an associated SMA is carried by the same optical fiber as each sensing region optical fiber.

16. The steerable force sensing catheter of claim 11 where each energy to an associated SMA is carried by a different optical fiber than each associated sensing region optical fiber.

17. The steerable force sensing catheter of claim 11 where each energy to an associated SMA is carried by an optical fiber having angled gratings which couple optical energy within said optical fiber to said associated SMA.

\* \* \* \* \*